(12) United States Patent
Kurata et al.

(10) Patent No.: US 11,585,761 B2
(45) Date of Patent: Feb. 21, 2023

(54) OH RADICAL MEASURING DEVICE AND OH RADICAL MEASURING METHOD

(71) Applicant: IHI CORPORATION, Tokyo (JP)

(72) Inventors: Takao Kurata, Tokyo (JP); Katsumi Takahashi, Tokyo (JP); Tsutomu Hayakawa, Tokyo (JP)

(73) Assignee: IHI CORPORATION, Tokyo (JP)

( * ) Notice: Subject to any disclaimer, the term of this patent is extended or adjusted under 35 U.S.C. 154(b) by 3 days.

(21) Appl. No.: 17/177,324

(22) Filed: Feb. 17, 2021

(65) Prior Publication Data

US 2021/0164909 A1 Jun. 3, 2021

Related U.S. Application Data

(63) Continuation of application No. PCT/JP2019/032709, filed on Aug. 21, 2019.

(30) Foreign Application Priority Data

Aug. 23, 2018 (JP) .............................. JP2018-156325

(51) Int. Cl.
 *G01N 21/78* (2006.01)
(52) U.S. Cl.
 CPC .................................. *G01N 21/783* (2013.01)
(58) Field of Classification Search
 CPC ...................................................... G01N 21/783
 See application file for complete search history.

(56) References Cited

U.S. PATENT DOCUMENTS

| 6,818,259 B1* | 11/2004 | Koontz .................. A61L 27/28 427/536 |
| 8,809,064 B2 | 8/2014 | Miller |
| 2004/0214340 A1 | 10/2004 | Kajii |
| 2014/0190436 A1 | 7/2014 | Inubushi et al. |
| 2015/0353382 A1 | 12/2015 | Murayama et al. |
| 2017/0122954 A1 | 5/2017 | Lebedeva et al. |
| 2019/0376903 A1 | 12/2019 | Kurata et al. |

FOREIGN PATENT DOCUMENTS

| CN | 101241076 A | 8/2008 |
| CN | 103149188 A | 6/2013 |
| EP | 2 941 955 A1 | 11/2015 |
| JP | 2003-075347 A | 3/2003 |

(Continued)

OTHER PUBLICATIONS

Louit et al, "The reaction of coumarin with the OH radical revisited: hydroxylation product analysis determined by fluorescence and chromatography", 2005, Radiation Physics and Chemistry, 72, 2-3, pp. 119-124 (Year: 2005).*

(Continued)

*Primary Examiner* — Matthew D Krcha
*Assistant Examiner* — Austin Q Le

(57) ABSTRACT

An OH radical measurement device includes a contact unit configured to bring an OH radical detection probe into contact with a gas to be measured, the OH radical detection probe including an aromatic carboxylic acid or an aromatic carboxylic acid derivative, a polar aprotic organic solvent, and a polar protic organic solvent having a content higher than a content of the polar aprotic organic solvent.

9 Claims, 3 Drawing Sheets

(56) References Cited

FOREIGN PATENT DOCUMENTS

| JP | 2008-128905 | A |   | 6/2008 |
| --- | --- | --- | --- | --- |
| JP | 2012-098114 | A |   | 5/2012 |
| JP | 2014-130105 | A |   | 7/2014 |
| JP | 2014-166969 | A |   | 9/2014 |
| JP | 5740138 | B2 |   | 6/2015 |
| JP | 2016-171792 | A |   | 9/2016 |
| JP | 2016173928 | A | * | 9/2016 |
| JP | 2016-185083 | A |   | 10/2016 |
| JP | 2018-040639 | A |   | 3/2018 |
| WO | 2013/024761 | A1 |   | 2/2013 |
| WO | 2018/155260 | A1 |   | 8/2018 |

OTHER PUBLICATIONS

Measurement of OH Radicals in Aqueous Solution Produced by Atmospheric-pressure LF Plasma Jet, 2012, International Journal of Plasma Environmental Science & Technology, 6, 2, pp. 166-171 (Year: 2012).*

Newton et al, Fluorescence detection of hydroxyl radicals, Radiation Physics and Chemistry, 2006, 75, pp. 473-478 (Year: 2006).*

Takanori Iijima et al., "OH Radical Generator for Waste Water Treatment Containing Recalcitrant Organic Matter", Toshiba Review vol. 61, No. 8, pp. 40-43 (2006).

International Search Report received for PCT Patent Application No. PCT/JP2019/032709, dated Oct. 21, 2019, 4 pages (2 pages of English translation and 2 pages of PCT search report).

V. Nahuel Montesinos et al., "Detection and quantification of reactive oxygen species (ROS) in indoor air," Talanta, vol. 138, 2015, pp. 20-27, Elsevier B.V.

Takayuki Morioka et al., "Kinetic study of self-decomposition of ozone by the extended SBH model", Journal of Japan Water Works Association, vol. 63, No. 11, pp. 28-30 (1994).

Shigeki Nakayama et al., "Generation of OH Radicals and Applied Technology", NTS, pp. 79, 187-188, and 202-203 (2008).

Safety Data Sheet (SDS): terephthalic acid, <online> http://www.st.rim.or.jp/~shw/MSDS/20034250.pdf, Aug. 31, 2020, Showa Chemical Co., Ltd.

Jose L. Sotelo et al., "Ozone Decomposition in Water: Kinetic Study," Industrial & Engineering Chemistry Research, vol. 26, pp. 39-43 (1987), ACS Publications.

* cited by examiner

OH RADICAL MEASURING DEVICE AND OH RADICAL MEASURING METHOD

CROSS REFERENCE TO RELATED APPLICATIONS

This application is a continuation application of International Application No. PCT/JP2019/032709, filed on Aug. 21, 2019, which claims priority to Japanese Patent Application No. 2018-156325 filed on Aug. 23, 2018, the entire contents of which are incorporated by reference herein.

BACKGROUND ART

Technical Field

The present disclosure relates to an OH radical measurement device and an OH radical measurement method.

As a technology for measuring an OH radical in water, a technology involving deriving a concentration of an OH radical by measuring a concentration of hydroxyterephthalic acid has hitherto been developed (for example, Patent Literature 1). The technology of Patent Literature 1 involves generating an OH radical by discharging an electric current in an aqueous solution containing terephthalic acid. In addition, the technology of Patent Literature 1 involves measuring a concentration of hydroxyterephthalic acid generated by a reaction between the generated OH radical and terephthalic acid.

CITATION LIST

Patent Literature

Patent Literature 1: JP 5740138 B2

SUMMARY

Technical Problem

As described in Patent Literature 1, a technology for detecting an OH radical in a liquid phase has hitherto been developed. However, a technology for detecting an OH radical in a gas phase has not been developed.

In view of the above-mentioned problem, an object of the present disclosure is to provide an OH radical measurement device and an OH radical measurement method, which are capable of detecting an OH radical in a gas phase.

Solution to Problem

In order to solve the above-mentioned problem, according to one embodiment of the present disclosure, there is provided an OH radical measurement device, including a contact unit configured to bring an OH radical detection probe into contact with a gas to be measured, the OH radical detection probe including an aromatic carboxylic acid or an aromatic carboxylic acid derivative, a polar aprotic organic solvent, and a polar protic organic solvent having a content higher than a content of the polar aprotic organic solvent.

In addition, the OH radical detection probe may include the polar protic organic solvent at a content that is more than 1 time and 16 times or less as high as a content of the polar aprotic organic solvent.

In addition, the polar protic organic solvent may be any one or a plurality of methanol, ethanol, and propanol.

In addition, the OH radical measurement device may further include: an irradiation unit configured to irradiate the OH radical detection probe after being brought into contact with the gas to be measured with UV light; a measurement unit configured to measure an intensity of fluorescence generated from the OH radical detection probe; and a concentration derivation unit configured to derive a concentration of an OH radical in the gas to be measured based on the intensity of the fluorescence measured by the measurement unit.

In order to solve the above-mentioned problem, according to one embodiment of the present disclosure, there is provided an OH radical measurement method, including measuring an OH radical in a gas to be measured through use of an OH radical detection probe including an aromatic carboxylic acid or an aromatic carboxylic acid derivative, a polar aprotic organic solvent, and a polar protic organic solvent having a content higher than a content of the polar aprotic organic solvent.

Effects of Disclosure

According to the present disclosure, the OH radical in the gas phase can be detected.

DESCRIPTION OF EMBODIMENTS

Figure 1:
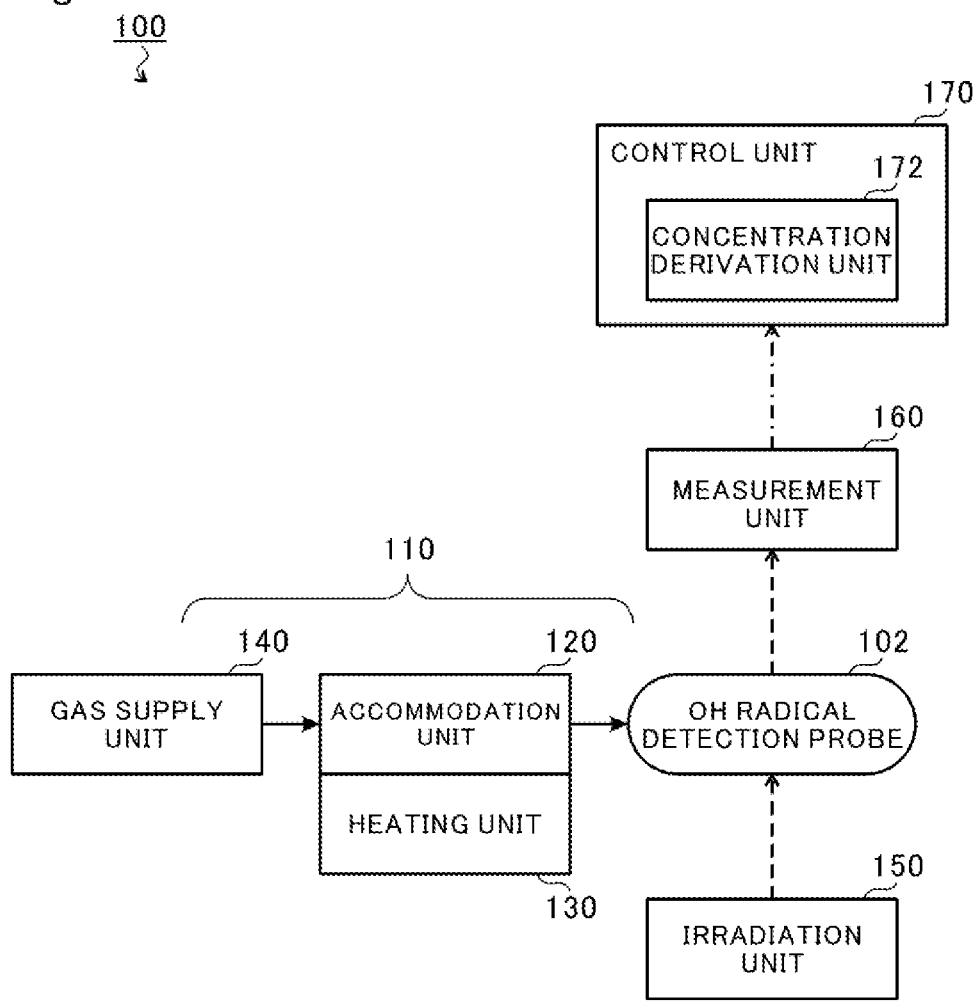
FIG. 1 is a diagram for illustrating an OH radical measurement device.

Now, with reference to the attached drawings, an embodiment of the present disclosure is described in detail. The dimensions, materials, and other specific numerical values represented in the embodiment are merely examples used for facilitating the understanding of the disclosure, and do not limit the present disclosure unless otherwise noted. Elements having substantially the same functions and configurations herein and in the drawings are denoted by the same reference symbols to omit redundant description thereof. In addition, illustration of elements with no direct relationship to the present disclosure is omitted.

[OH Radical Detection Probe]

An OH radical detection probe according to this embodiment includes an aromatic carboxylic acid or an aromatic carboxylic acid derivative (hereinafter collectively referred to as "aromatic carboxylic acids"), a polar aprotic organic solvent, and a polar protic organic solvent. When the OH radical detection probe includes the polar protic organic solvent, the aromatic carboxylic acids and an OH radical can be caused to react with each other, and thus the OH radical can be detected.

In addition, a related-art OH radical detection probe configured to measure an OH radical in a liquid phase is an aqueous solution that uses water as a solvent for dissolving terephthalic acid. Therefore, when an attempt is made to measure an OH radical in a gas phase, in particular, water vapor (or in a humidified gas phase having a high humidity) with the related-art OH radical detection probe, an OH radical generated from an OH radical precursor dissolved in the aqueous solution of the probe itself and terephthalic acid preferentially react with each other. Therefore, with the related-art OH radical detection probe, the OH radical generated from the aqueous solution of the probe itself and the OH radical in the gas phase cannot be discriminated from each other. Thus, the related-art OH radical detection probe has a problem in that the OH radical in the gas phase cannot be selectively and quantitatively detected.

In contrast, the OH radical detection probe according to this embodiment is a non-aqueous solvent including the polar aprotic organic solvent as a main solvent. Therefore, the OH radical detection probe according to this embodiment eliminates the generation of an OH radical caused by dissolution of an OH radical precursor in a liquid phase (when there is no moisture, an OH radical is not generated (Shigeki Nakayama et al., Generation of OH Radicals and Applied Technology NTS, pp. 191-217 (2008), J. A. Roth, D. E. Sullivan: Kinetics of ozone decomposition in water: Kinetic study, Ind. Eng. Chem. Res., 26, pp. 39-43 (1987), Takayuki Morioka et al.: Kinetic study of self-decomposition by the extended SBH model, Journal of Japan Water Works Association, vol. 63, No. 11, pp. 28-40 (1994))). Thus, the OH radical detection probe according to this embodiment can prevent the situation in which the OH radical generated from the OH radical precursor dissolved in the liquid phase and the aromatic carboxylic acids react with each other, unlike an aqueous solvent (aqueous solution).

In addition, when the OH radical and the aromatic carboxylic acids react with each other, a proton (Hi) is generated. Therefore, when only the polar aprotic organic solvent is used as an organic solvent for dissolving the aromatic carboxylic acids, the proton is not accepted, and the reaction between the OH radical and the aromatic carboxylic acids will be not able to proceed.

In view of the foregoing, the OH radical detection probe according to this embodiment includes the polar protic organic solvent as a sub-solvent, and hence the proton generated by the reaction can be accepted. With this, the OH radical detection probe according to this embodiment is able to allow the reaction between the OH radical and the aromatic carboxylic acids to proceed, thereby being capable of generating a hydroxy form of the aromatic carboxylic acids, with the result that the OH radical in the gas phase can be detected. In particular, the OH radical detection probe according to this embodiment can detect an OH radical in water vapor or in a humidified gas phase having a high humidity. In this case, the "gas phase" has a concept encompassing a gas containing a liquid (for example, liquid water) as well as a phase in which only a gas is present. The gas containing a liquid is a gas containing a mist, a gas including a liquid layer (for example, a gas including portions in which water molecules are formed into a plurality of layers), or a gas in which a liquid is dispersed (aerosol).

In addition, the aromatic carboxylic acids forming the OH radical detection probe according to this embodiment are one or a plurality of compounds selected from the group consisting of phthalic acid (o-phthalic acid, m-phthalic acid, and p-phthalic acid (terephthalic acid)), derivatives of phthalic acid (for example, dimethyl terephthalate), benzoic acid, derivatives of benzoic acid (for example, hydroxybenzoic acid (2-hydroxybenzoic acid (salicylic acid), 3-hydroxybenzoic acid, and 4-hydroxybenzoic acid)), and a compound in which a carboxy group or a carbonyl group is bonded to a benzene ring through a substituent (e.g., coumarin (abbreviation: Cou), coumarin-3-carboxylic acid (abbreviation: CCA), or phenylalanine). The aromatic carboxylic acid is preferably one or a plurality of compounds selected from the group consisting of terephthalic acid, salicylic acid, 4-hydroxybenzoic acid, coumarin, and phenylalanine. It is preferred that the aromatic carboxylic acid forming the OH radical detection probe be terephthalic acid that is inexpensive and is easily available. In addition, the above-mentioned aromatic carboxylic acids other than terephthalic acid have characteristics of specifically (selectively) reacting with OH radicals in the same manner as in terephthalic acid. Therefore, the above-mentioned aromatic carboxylic acids other than terephthalic acid may be included in the OH radical detection probe instead of or in addition to terephthalic acid.

In addition, the polar aprotic organic solvent forming the OH radical detection probe according to this embodiment is, for example, one or a plurality of compounds selected from the group consisting of N,N-dimethylformamide (DMF), tetrahydrofuran (THF), acetone, acetonitrile, dimethyl sulfoxide (DMSO), dioxane, chloroform, ethylene dichloride, and methylene chloride. The polar aprotic organic solvent is a polar organic solvent that does not donate a proton. Therefore, when the polar aprotic organic solvent is incorporated into the OH radical detection probe instead of water, the reaction in which the OH radical precursor in the liquid becomes an OH radical can be stopped. In addition, the polar aprotic organic solvent can easily dissolve aromatic carboxylic acids and the like. That is, it is only required that the polar aprotic organic solvent be capable of dissolving the aromatic carboxylic acids in the liquid (http://www.st.rim.or.jp/~shw/MSDS/20034250.pdf). In addition, the polar aprotic organic solvent preferably has a relatively large specific dielectric constant. For example, one or a plurality of solvents selected from the group consisting of DMF, DMSO, and acetonitrile are preferred.

In addition, the polar protic organic solvent forming the OH radical detection probe according to this embodiment is one or a plurality of compounds selected from the group consisting of methanol, ethanol, 1-propanol, 2-propanol (isopropanol), acetic acid, ethyl acetate, formic acid, 1-butanol, isobutyl alcohol, ethylene glycol, and methanediol. The polar protic organic solvent is a polar organic solvent that donates a proton. Therefore, when the polar protic organic solvent is incorporated into the OH radical detection probe, a proton generated by the reaction can be accepted in the OH radical detection probe. Then, the reaction represented by the following reaction formula (1) proceeds. That is, in order to allow the reaction formula (1) to proceed, the polar protic organic solvent is incorporated into the OH radical detection probe.

Reaction formula (1)

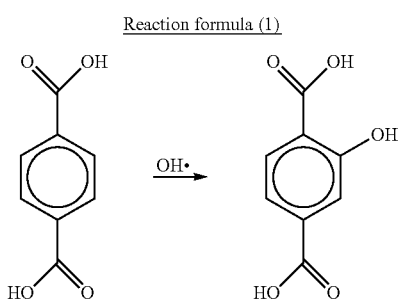

The reaction formula (1) may also be expressed as terephthalic acid+OH radical→2-hydroxyterephthalic acid (HTA)+proton.

The polar protic organic solvent included in the OH radical detection probe preferably has a relatively large specific dielectric constant.

[OH Radical Measurement Device 100]

Next, an OH radical measurement device 100 using the above-mentioned OH radical detection probe is described. FIG. 1 is a diagram for illustrating the OH radical measurement device 100. In FIG. 1, the solid arrows indicate the flow of a gas or a liquid, the dashed arrows indicate the flow of light, and the dashed-dotted arrow indicates the flow of a signal.

As illustrated in FIG. 1, the OH radical measurement device 100 includes a contact unit 110, an irradiation unit 150, a measurement unit 160, and a control unit 170.

The contact unit 110 is configured to bring the OH radical detection probe into contact with a gas to be measured. The contact unit 110 includes an accommodation unit 120, a heating unit 130, and a gas supply unit 140.

The accommodation unit 120 is a container configured to accommodate an OH radical detection probe 102 (liquid) described above. The heating unit 130 is configured to heat the gas to be measured and the OH radical detection probe 102 in the accommodation unit 120 to a predetermined temperature when the humidity in a gas phase is high. The gas supply unit 140 is configured to supply the gas to be measured into the accommodation unit 120.

Figure 2:
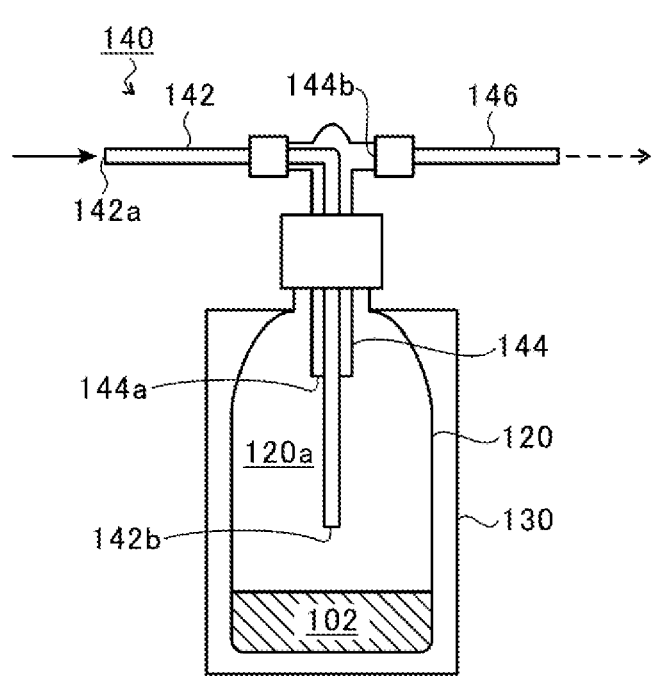
FIG. 2 is a view for illustrating a specific configuration of an accommodation unit, a heating unit, and a gas supply unit.

FIG. 2 is a view for illustrating a specific configuration of the accommodation unit 120, the heating unit 130, and the gas supply unit 140. In FIG. 2, the solid arrow indicates the flow of the gas to be measured, and the dashed arrow indicates the flow of the gas after contact. As illustrated in FIG. 2, the accommodation unit 120 is a sealed container. The OH radical detection probe 102 is accommodated in an inner space 120a of the accommodation unit 120.

The heating unit 130 is configured to heat the gas to be measured and the OH radical detection probe 102 in the accommodation unit 120 when the gas to be measured has a high humidity. The heating unit 130 is formed of, for example, a heater surrounding the accommodation unit 120. With the configuration including the heating unit 130, when the gas to be measured has a high humidity, the situation in which moisture is condensed to generate liquid water can be prevented in the accommodation unit 120.

The gas supply unit 140 includes an inner pipe 142, an outer pipe 144, and an exhaust pipe 146. The inner pipe 142 is a pipe having one end 142a connected to a gas supply source (not shown) and another end 142b arranged in the inner space 120a of the accommodation unit 120. The outer pipe 144 is a pipe surrounding part of the inner pipe 142. The outer pipe 144 is a pipe having one end 144a arranged in the inner space 120a of the accommodation unit 120 and another end 144b connected to the exhaust pipe 146. The other end 142b of the inner pipe 142 is positioned vertically below (on an OH radical detection probe 102 side of) the one end 144a of the outer pipe 144.

Thus, the gas to be measured, which has been supplied by the gas supply unit 140, reaches the inner space 120a of the accommodation unit 120 from the other end 142b of the inner pipe 142. Then, the gas to be measured flows into the outer pipe 144 from the one end 144a of the outer pipe 144 after being brought into contact with the OH radical detection probe 102 in the inner space 120a. The gas to be measured, which has flowed into the outer pipe 144, is discharged to the outside through the exhaust pipe 146.

Returning to FIG. 1, the irradiation unit 150 is configured to irradiate the OH radical detection probe 102 (after being brought into contact with the gas to be measured) taken out of the accommodation unit 120 with UV light (for example, UV light having a wavelength of 310 nm). The measurement unit 160 is configured to measure the intensity of fluorescence (for example, a peak of fluorescence having a wavelength of 425 nm or a wavelength in the vicinity of 425 nm indicating hydroxyterephthalic acid (hereinafter referred to as "HTA") that is the hydroxy form of aromatic carboxylic acids) generated from the OH radical detection probe 102 through the irradiation with UV light by the irradiation unit 150.

The control unit 170 is formed of a semiconductor integrated circuit including a central processing unit (CPU). The control unit 170 is configured to read a program, a parameter, and the like for operating the CPU itself from a ROM, and to manage and control the entire OH radical measurement device 100 in cooperation with a RAM and other electronic circuits serving as a work area. In this embodiment, the control unit 170 functions as a concentration derivation unit 172.

The concentration derivation unit 172 is configured to derive the concentration of the OH radical in the gas to be measured based on the intensity of the fluorescence measured by the measurement unit 160.

For example, in the case where terephthalic acid is adopted as the aromatic carboxylic acid forming the OH radical detection probe 102, when the OH radical in the gas phase is bonded to the OH radical detection probe 102, the reaction represented by the reaction formula (1) proceeds.

Thus, in this case, terephthalic acid reacts with the OH radical to generate 2-hydroxyterephthalic acid (HTA) and a proton. Therefore, when the OH radical detection probe 102 is irradiated with UV light by the irradiation unit 150, fluorescence is generated from HTA. Then, the measurement unit 160 measures the intensity of fluorescence generated from HTA (fluorescence intensity), with the result that the concentration of HTA, that is, the concentration of the OH radical in the gas phase (in the gas to be measured) can be calculated based on the fluorescence intensity.

Thus, a calibration curve of the fluorescence intensity of HTA can be created by preparing a plurality of reference solutions having different concentrations, and next irradiating each of the solutions with UV light to measure a fluorescence intensity. Therefore, the concentration derivation unit 172 can derive the concentration of the OH radical based on the fluorescence intensity measured by the measurement unit 160 and the calibration curve.

Incidentally, it is conceivable that, in order to improve detection sensitivity of an OH radical by the OH radical detection probe 102, the concentration of the aromatic carboxylic acids in the OH radical detection probe 102 is increased.

However, the wavelength of fluorescence generated from the hydroxy form of the aromatic carboxylic acids is close to the wavelength of fluorescence generated from the aromatic carboxylic acids. Specifically, the wavelength of fluorescence generated from HTA that is the hydroxy form of the aromatic carboxylic acids has a peak at 425 nm or in the vicinity of 425 nm, and the wavelength of fluorescence generated from terephthalic acid that belongs to the aromatic carboxylic acids has a peak at 340 nm or in the vicinity of 340 nm. Therefore, when the concentration of terephthalic acid in the OH radical detection probe 102 is increased, the width of a peak indicating the intensity of fluorescence generated from unreacted terephthalic acid is increased, and a peak bottom portion is enlarged. Then, a peak indicating the intensity of fluorescence generated from HTA in the OH radical detection probe 102 is buried in the peak of the unreacted terephthalic acid. Thus, there is a problem in that, even when the concentration of the aromatic carboxylic acids in the OH radical detection probe 102 is increased, the intensity of fluorescence generated from HTA cannot be accurately measured or fluorescence generated from HTA cannot be measured.

In general, a molecule in an electronically excited state has an electric dipole moment different from that in an electronic ground state. Therefore, in a polar solvent, reorientation of solvent molecules may occur in the excited state so as to stabilize the dipole moment of the excited molecules. As a result, for example, the following is observed. The excited state is relatively stabilized. A fluorescence spectrum is shifted to a longer wavelength. The fluorescence lifetime is extended. Therefore, the peak of the wavelength of the fluorescence generated from HTA in the OH radical detection probe 102 is 425 nm or is shifted to the longer wavelength side by a predetermined wavelength from 425 nm. Similarly, the peak of the wavelength of the fluorescence generated from terephthalic acid in the OH radical detection probe 102 is 340 nm or is shifted to the longer wavelength side by a predetermined wavelength from 340 nm.

In view of the foregoing, in the OH radical detection probe 102 according to this embodiment, the content of the polar protic organic solvent is set to be higher than that of the polar aprotic organic solvent. That is, the OH radical detection probe 102 according to this embodiment includes an aromatic carboxylic acid or an aromatic carboxylic acid derivative, a polar aprotic organic solvent, and a polar protic organic solvent having a content higher than that of the polar aprotic organic solvent.

When the content of the polar protic organic solvent is set to be higher than that of the polar aprotic organic solvent, the polarizability of the OH radical detection probe 102 can be increased with the polar protic organic solvent. With this, the OH radical detection probe 102 can increase the reaction conversion rate between the OH radical and the aromatic carboxylic acids, and as a result, can increase the generation amount of the hydroxy form of the aromatic carboxylic acids. Therefore, the OH radical detection probe 102 can increase the fluorescence intensity of the hydroxy form of the aromatic carboxylic acids without increasing the amount of the aromatic carboxylic acids. Therefore, the OH radical detection probe 102 can improve the detection sensitivity of the hydroxy form of the aromatic carboxylic acids (OH radical).

When the content of the polar protic organic solvent is more than 16 times as high as that of the polar aprotic organic solvent, the solubility of the aromatic carboxylic acids decreases. Therefore, the OH radical detection probe 102 includes the polar protic organic solvent at a content that is more than 1 time and 16 times or less as high as that of the polar aprotic organic solvent. The OH radical detection probe 102 preferably includes the polar protic organic solvent at a content that is more than 1 time and 8 times or less as high as that of the polar aprotic organic solvent. With this, the OH radical detection probe 102 can increase the fluorescence intensity of the hydroxy form of the aromatic carboxylic acids while maintaining the solubility of the aromatic carboxylic acids.

In addition, the concentration of the aromatic carboxylic acid in the solvent (polar aprotic organic solvent and polar protic organic solvent) in the OH radical detection probe 102 is, for example, preferably 0.02 mmol/L (0.02 mM=0.02 mol/m$^3$) or more and 20 mmol/L (20 mM=20 mol/m$^3$) or less, and more preferably falls within a range of 0.2 mmol/L or more and 2 mmol/L or less.

In addition, the polar protic organic solvent included in the OH radical detection probe 102 is one or a plurality of methanol, ethanol, and propanol. When, as the polar protic organic solvent included in the OH radical detection probe 102, a monohydric alcohol in which the number of carbon atoms in a hydrocarbon portion having an OH group (hydroxy group) is reduced (that is, the polarization (dielectric constant) is increased) is used, a strongly polarized protic polar organic solvent can be obtained. With this, the OH radical detection probe 102 can increase the fluorescence intensity of the hydroxy form of the aromatic carboxylic acids. In the polar protic organic solvent, the degree of polarization is indicated by a dielectric constant (specific dielectric constant). When the dielectric constant is larger, the degree of polarization is increased.

In addition, the polar protic organic solvent included in the OH radical detection probe 102 is preferably propanol (1-propanol or 2-propanol), more preferably ethanol, and most preferably methanol. When the volume ratio of the OH group (hydroxy group) in all the atoms forming the polar protic organic solvent is higher, stronger polarization is exhibited, and hence a stronger polar solvent is obtained. Therefore, the OH radical detection probe 102 can increase the fluorescence intensity of the hydroxy form of the aromatic carboxylic acids while maintaining the solubility of the aromatic carboxylic acids.

[OH Radical Measurement Method]

Figure 3:
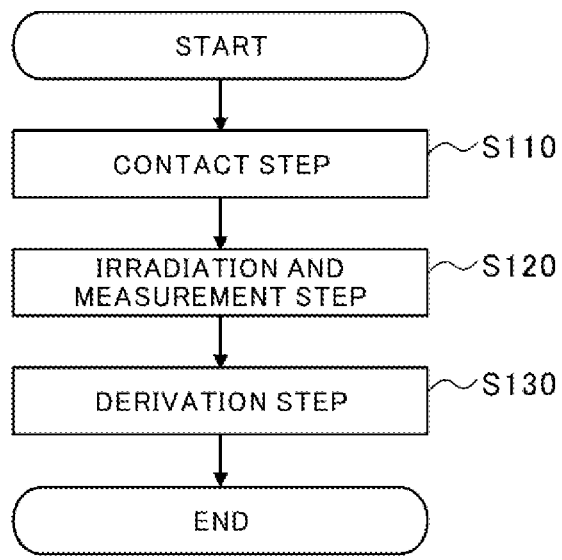
FIG. 3 is a flowchart for illustrating a flow of processing of an OH radical measurement method.

Subsequently, an OH radical measurement method using the OH radical measurement device 100 is described. FIG. 3 is a flowchart for illustrating a flow of processing of the OH radical measurement method. The OH radical measurement method includes a contact step S110, an irradiation and measurement step S120, and a derivation step S130.

[Contact Step S110]

The contact step S110 is a step of bringing the OH radical detection probe 102 and the gas to be measured into contact with each other under a predetermined temperature. Specifically, first, the OH radical detection probe 102 is accommodated in the accommodation unit 120. Then, when the gas to be measured is supplied to the inner space 120a of the accommodation unit 120 by the gas supply unit 140, the OH radical detection probe 102 and the gas to be measured are brought into contact with each other. When the gas to be measured has a high humidity, the gas to be measured and the OH radical detection probe 102 in the accommodation unit 120 are heated to a predetermined temperature by driving the heating unit 130.

[Irradiation and Measurement Step S120]

In the irradiation and measurement step S120, first, the OH radical detection probe 102 after being brought into contact with the gas to be measured in the contact step S110 is taken out. Then, the irradiation unit 150 irradiates the OH radical detection probe 102 thus taken out with UV light, and the measurement unit 160 measures the intensity of fluorescence generated from the OH radical detection probe 102.

[Derivation Step S130]

The derivation step S130 is a step in which the concentration derivation unit 172 derives the concentration of the OH radical in the gas to be measured based on the intensity of the fluorescence measured in the irradiation and measurement step S120.

As described above, according to the OH radical measurement device 100 of this embodiment and the OH radical measurement method using the OH radical measurement device 100, through use of an organic solvent other than water as a solvent of the OH radical detection probe 102, an OH radical in a gas phase can be measured.

First Example

An OH radical detection probe of each of Examples A to D was prepared. Then, 5 mL of Example A having one drop of a hydrogen peroxide solution dropped thereto, 5 mL of Example B having one drop of a hydrogen peroxide solution dropped thereto, 5 mL of Example C having one drop of a hydrogen peroxide solution dropped thereto, and 5 mL of Example D having one drop of a hydrogen peroxide solution dropped thereto were each irradiated with UV light, and the intensity of fluorescence (fluorescence intensity of a peak at 425 nm or in the vicinity of 425 nm) of HTA generated from each of Examples A to D was measured. Then, the concentration ($\mu$M) of HTA was derived based on the measured intensity of fluorescence.

Example A is a solution obtained by dissolving 0.2 mmol/L of terephthalic acid in DMF. Example B is a solution obtained by dissolving 0.2 mmol/L of terephthalic acid in DMF and 2-propanol (volume ratio: 1:1). Example C is a solution obtained by dissolving 0.2 mmol/L of terephthalic acid in DMF and ethanol (volume ratio: 1:1). Example D is a solution obtained by dissolving 0.2 mmol/L of terephthalic acid in DMF and methanol (volume ratio: 1:1).

Figure 4:
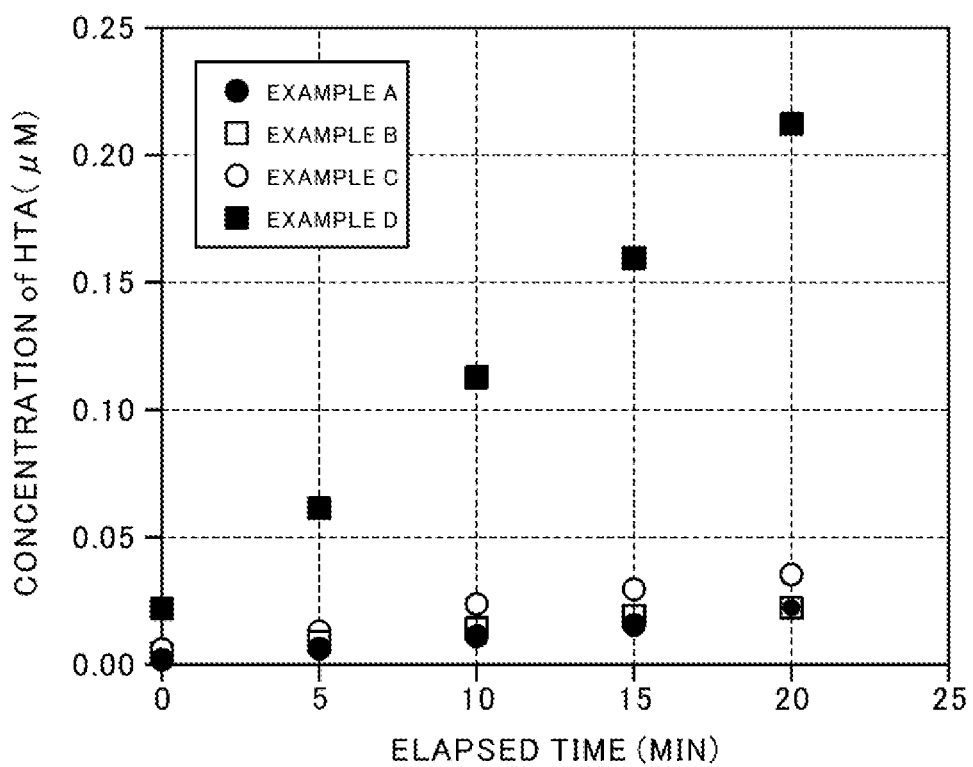
FIG. 4 is a graph for showing a relationship between the elapsed time after a hydrogen peroxide solution is dropped to each of Examples A to D and the concentration of HTA in each of Examples A to D.

FIG. 4 is a graph for showing a relationship between the elapsed time after the hydrogen peroxide solution is dropped to each of Examples A to D and the concentration of HTA in each of Examples A to D. In FIG. 4, the horizontal axis represents the elapsed time (min), and the vertical axis represents the concentration ($\mu$M) of HTA. In FIG. 4, the solid circles indicate Example A, the blank squares indicate Example B, the blank circles indicate Example C, and the solid squares indicate Example D.

As shown in FIG. 4, it was found that, in each of Examples A to D, the concentration of HTA (generation amount of HTA) was increased when the elapsed time became longer.

In addition, it was recognized that Example D had the highest generation rate of HTA (generation amount of HTA per unit time), and Example C had the second highest generation rate of HTA. Further, it was found that the generation rate of HTA in Example B was lower than that in Example C and higher than that in Example A.

From the above-mentioned results, it was recognized that Example D was able to detect an OH radical (HTA) with the most satisfactory sensitivity even when the generation amount of an OH radical was the same. That is, it was found that, through use of methanol as the polar protic organic solvent included in the OH radical detection probe, an OH radical can be detected with the most satisfactory sensitivity.

Second Example

An OH radical detection probe of each of Examples E to G was prepared and accommodated in the accommodation unit 120. In addition, as a gas to be measured, 600 ppm of ozone (diluted with oxygen) was supplied to the accommodation unit 120 at 1 L/min with water vapor of 46 $\mu$L/min. In Second Example, the heating by the heating unit 130 was performed at 145° C. Then, each of Examples E to G having a mixed gas of ozone and water vapor brought into contact therewith was irradiated with UV light, and the intensity of fluorescence (fluorescence intensity of a peak at 425 nm or in the vicinity of 425 nm) of HTA generated from each of Examples E to G was measured.

Example E is a solution obtained by dissolving 0.2 mmol/L of terephthalic acid in DMF and methanol (volume ratio: 1:1). Example F is a solution obtained by dissolving 0.2 mmol/L of terephthalic acid in DMF and methanol (volume ratio: 1:4). Example G is a solution obtained by dissolving 0.2 mmol/L of terephthalic acid in DMF and methanol (volume ratio: 1:8).

Figure 5:
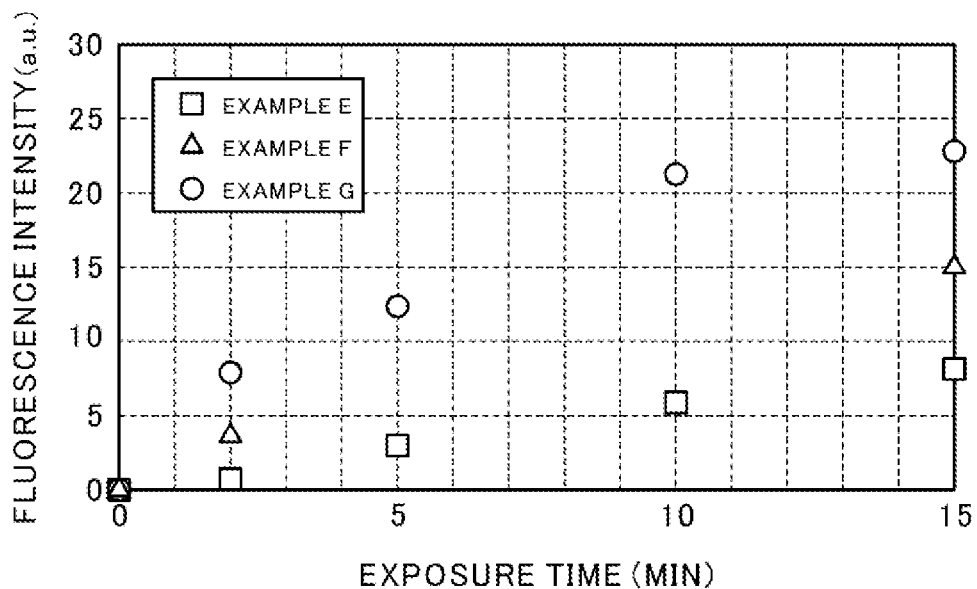
FIG. 5 is a graph for showing a relationship between the exposure time of a gas to be measured to each of Examples E to G and the fluorescence intensity of HTA.

FIG. 5 is a graph for showing a relationship between the exposure time of the gas to be measured to each of Examples E to G and the fluorescence intensity of HTA. In FIG. 5, the horizontal axis represents the exposure time (min), and the vertical axis represents the fluorescence intensity (a.u.) of HTA. In addition, in FIG. 5, the blank squares indicate Example E, the blank triangles indicate Example F, and the blank circles indicate Example G.

As shown in FIG. 5, it was found that, in each of Examples E to G, the fluorescence intensity of HTA was increased when the exposure time became longer.

In addition, it was recognized that Example G had the highest fluorescence intensity of HTA, and Example F had the second highest fluorescence intensity of HTA. Further, it was found that the fluorescence intensity of HTA in Example E was lower than that in Example F.

From the above-mentioned results, it was recognized that Example G was able to detect an OH radical (HTA) with the most satisfactory sensitivity even when the generation amount of an OH radical was the same. That is, it was found that, when the content of the polar protic organic solvent included in the OH radical detection probe is higher, an OH radical can be detected with higher sensitivity.

Third Example

Example H was obtained by exposing a gas to be measured for 4 minutes to 5 mL of a solution in which 0.2 mmol/L of terephthalic acid was dissolved in DMF and methanol (volume ratio: 1:8) accommodated in a petri dish (accommodation unit). Example I was obtained by exposing a gas to be measured to 10 mL of a solution in which 0.2 mmol/L of terephthalic acid was dissolved in DMF and methanol (volume ratio: 1:8) accommodated in a petri dish for 4 minutes. Example J was obtained by exposing a gas to be measured to 5 mL of a solution in which 0.2 mmol/L of terephthalic acid was dissolved in DMF and methanol (volume ratio: 1:4) accommodated in a petri dish for 4 minutes. Example K was obtained by exposing a gas to be measured to 10 mL of a solution in which 0.2 mmol/L of terephthalic acid was dissolved in DMF and methanol (volume ratio: 1:4) accommodated in a petri dish for 4 minutes. The gas to be measured is 500 ppm of a hydrogen peroxide gas. In addition, the petri dishes used in Examples H to K have the same shape. Then, each of Examples H to K having the gas to be measured brought into contact therewith was irradiated with UV light, and the intensity of fluorescence (fluorescence intensity of a peak at 425 nm or in the vicinity of 425 nm) of HTA generated from each of Examples H to K was measured.

Figure 6:
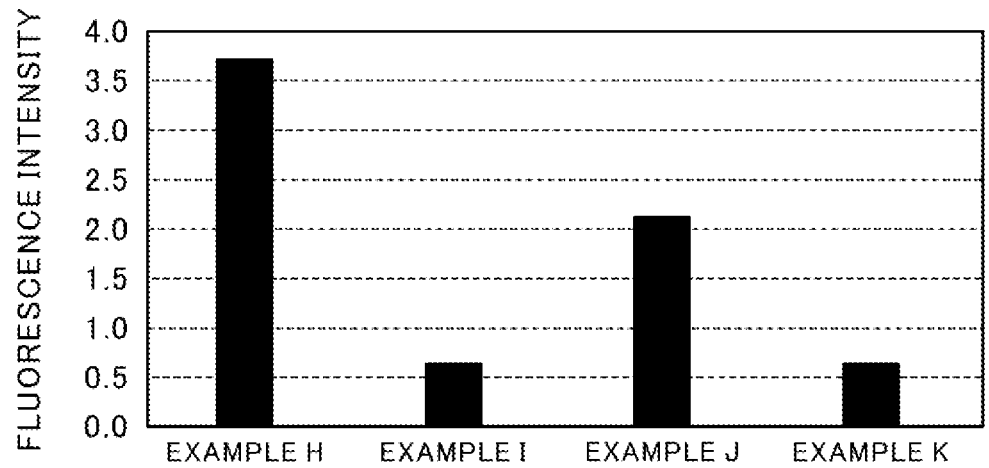
FIG. 6 is a graph for showing the fluorescence intensity of HTA in each of Examples H to K.

FIG. 6 is a graph for showing the fluorescence intensity of HTA in each of Examples H to K. As shown in FIG. 6, it was found that the fluorescence intensity of HTA in Example H was higher than that in Example J. That is, it was found that, in the same manner as in Second Example described above, when the content of the polar protic organic solvent included in the OH radical detection probe is higher, an OH radical can be detected with higher sensitivity.

In addition, as shown in FIG. 6, it was found that the fluorescence intensity of HTA in Example H was higher than that in Example I. Similarly, it was found that the fluorescence intensity of HTA in Example J was higher than that in Example K.

From the above-mentioned results, it was found that, when the volume accommodated in the accommodation unit is smaller, an OH radical can be detected with higher sensitivity even with the same OH radical detection probe. That is, it was recognized that, in the OH radical detection probe, when the contact area with the gas to be measured per unit volume is larger, an OH radical can be detected with higher sensitivity.

The embodiment of the present disclosure has been described above with reference to the attached drawings, but, needless to say, the present disclosure is not limited to the embodiment. It is apparent that those skilled in the art may arrive at various alterations and modifications within the scope of claims, and those examples are construed as naturally falling within the technical scope of the present disclosure.

For example, in the above-mentioned embodiment, the description has been made taking as an example the configuration in which the OH radical detection probe configured to generate a fluorescent compound through a reaction with an OH radical includes an aromatic carboxylic acid. However, the OH radical detection probe may include a chemical substance that generates a fluorescent compound other than the aromatic carboxylic acid.

In addition, in the above-mentioned embodiment, the description has been made taking as an example the case in which the OH radical detection probe includes only the aromatic carboxylic acid, the polar aprotic organic solvent, and the polar protic organic solvent. However, the OH radical detection probe is only required to be free of water, and the OH radical detection probe may include another solvent.

In addition, in the above-mentioned embodiment, the description has been made taking as an example the configuration in which the OH radical measurement device 100 includes the heating unit 130. However, the heating unit 130 is not an essential component.

INDUSTRIAL APPLICABILITY

The present disclosure is applicable to an OH radical measurement device and an OH radical measurement method.

What is claimed is:

1. An OH radical measurement device, comprising:
an OH radical detection probe; and
a contact unit configured to bring the OH radical detection probe into contact with a gas to be measured;
wherein
the OH radical detection probe is a mixture including
an aromatic carboxylic acid or an aromatic carboxylic acid derivative,
a polar aprotic organic solvent, and
a polar protic organic solvent having a content higher than a content of the polar aprotic organic solvent, and
the contact unit includes an accommodation unit and a gas supply unit.

2. The OH radical measurement device according to claim 1, wherein the content of the polar protic organic solvent included in the mixture of the OH radical detection probe is not more than 16 times the content of the polar aprotic organic solvent.

3. The OH radical measurement device according to claim 1, wherein the polar protic organic solvent is any one or a plurality of methanol, ethanol, and propanol.

4. The OH radical measurement device according to claim 2, wherein the polar protic organic solvent is any one or a plurality of methanol, ethanol, and propanol.

5. The OH radical measurement device according to claim 1, further comprising:
an irradiation unit configured to irradiate the OH radical detection probe after being brought into contact with the gas to be measured with UV light;
a measurement unit configured to measure an intensity of fluorescence generated from the OH radical detection probe; and
a central processing unit (CPU) configured to derive a concentration of an OH radical in the gas to be measured based on the intensity of the fluorescence measured by the measurement unit.

6. The OH radical measurement device according to claim 2, further comprising:
an irradiation unit configured to irradiate the OH radical detection probe after being brought into contact with the gas to be measured with UV light;
a measurement unit configured to measure an intensity of fluorescence generated from the OH radical detection probe; and
a central processing unit (CPU) configured to derive a concentration of an OH radical in the gas to be measured based on the intensity of the fluorescence measured by the measurement unit.

7. The OH radical measurement device according to claim 3, further comprising:
an irradiation unit configured to irradiate the OH radical detection probe after being brought into contact with the gas to be measured with UV light;
a measurement unit configured to measure an intensity of fluorescence generated from the OH radical detection probe; and
a central processing unit (CPU) configured to derive a concentration of an OH radical in the gas to be measured based on the intensity of the fluorescence measured by the measurement unit.

8. The OH radical measurement device according to claim 4, further comprising:
an irradiation unit configured to irradiate the OH radical detection probe after being brought into contact with the gas to be measured with UV light;

a measurement unit configured to measure an intensity of fluorescence generated from the OH radical detection probe; and a central processing unit (CPU) configured to derive a concentration of an OH radical in the gas to be measured based on the intensity of the fluorescence measured by the measurement unit.

9. An OH radical measurement method, comprising measuring an OH radical in a gas to be measured through use of an OH radical detection probe, which is a mixture including an aromatic carboxylic acid or an aromatic carboxylic acid derivative, a polar aprotic organic solvent, and a polar protic organic solvent having a content higher than a content of the polar aprotic organic solvent.

* * * * *